United States Patent [19]

Broad, Jr.

[11] Patent Number: 4,972,850
[45] Date of Patent: Nov. 27, 1990

[54] NO HANDS CONTRACEPTIVE DEVICE

[76] Inventor: Robert L. Broad, Jr., 2300 Brookwood Dr., SE., Decatur, Ala. 35601

[21] Appl. No.: 300,140

[22] Filed: Jan. 23, 1989

[51] Int. Cl.$^5$ ............................................. A61F 6/04
[52] U.S. Cl. .................................. 128/844; 128/842; 604/349
[58] Field of Search ........................... 128/842, 844; 604/347-352

[56] References Cited

U.S. PATENT DOCUMENTS

| 4,731,064 | 3/1988 | Heyden ......................... 604/352 |
| 4,872,463 | 10/1989 | Nishizono ..................... 128/844 |

FOREIGN PATENT DOCUMENTS

| 162728 | 9/1905 | Fed. Rep. of Germany ...... 604/349 |
| 36015 | 1/1909 | Fed. Rep. of Germany ...... 604/349 |
| 111720 | 12/1928 | Fed. Rep. of Germany ...... 604/349 |
| 2410697 | 6/1974 | Fed. Rep. of Germany. |
| 8802624 | 4/1988 | World Int. Prop. O. .......... 604/349 |

Primary Examiner—Robert A. Hafer
Assistant Examiner—Kevin G. Rooney

[57] ABSTRACT

A no hands contraceptive device wherein a condom having a rolled portion is provided with a pair of strips positioned on opposite sides of the condom, each of the strips having one end thereof rolled into the rolled portion of the condom and the other end thereof extending from the rolled portion of the condom such that when the strips are pulled the condom will unroll onto the user's penis without being touched by the user's hands. The strips have a width which is sufficiently great to cause the rolled portion of the condom to assume a generally elliptical configuration having a length to width ratio of at least 1.2 to prevent premature unrolling and the tangling of the condom which may occur when the condom partially unrolls prematurely.

18 Claims, 6 Drawing Sheets

PRIOR ART DEVICE

FIG. 1

PRIOR ART DEVICE

NO HANDS CONTRACEPTIVE DEVICE

BACKGROUND

1. Field of the Invention

This invention relates to contraceptive devices.

2. Prior Art

Condoms are not only used to prevent conception but also serve another useful purpose in that they inhibit the spread of a number of sexually transmitted diseases.

Most of the condoms now on the market are purchased in a sealed packet and are liberally coated with a lubricant. The user tears open the packet, removes the condom and then, using his hands, unrolls the condom onto his penis. One disadvantage of this is that the user cannot avoid having a large part of the lubricant wind up on his hands, an undesirable situation. Also, lubricated condoms are very slippery. This makes them difficult to put on and causes the donning to require an excessive amount of time. These problems have existed for decades.

Further, it is understood that if a person who is infected with Acquired Immune Deficiency Syndrome (AIDS) has a cut or open sore on his hand, his use of a conventional condom may not substantially lessen the possibility that he will transmit the AIDS virus to his sexual partner. The reason for this is that it is impossible for him to put on a conventional condom without touching it with his hands, so that the AIDS virus from body fluids from the cut or sore can contaminate the condom when it is touched as it is put on.

West German Offenlegungsschrift No. 2,410,697 discloses a condom into which is rolled a pair of strands or strips which are pulled to unroll the condom. Applicant has discovered a major problem which frequently occurs when a device such as that disclosed in this German application is used in a certain manner.

SUMMARY OF THE INVENTION

A no hands contraceptive device made up of a condom having a rolled portion and a pair of strips positioned on opposite sides of the condom, the strips each having one end thereof rolled into the rolled portion of the condom and the other end thereof extending from the rolled portion of the condom such that the condom can be unrolled onto the penis by pulling the strips. The strips have a width which is sufficiently great to cause the rolled portion of the condom to assume a generally elliptical configuration having a length to width ratio of at least 1.2 to significantly increase the resistance of the condom to unrolling and to thereby prevent premature unrolling and the tangling of the condom which is likely to occur when the condom unrolls prematurely.

DETAILED DESCRIPTION OF THE INVENTION

West German Offenlegungsschrift No. 2,410,697 discloses a pair of strands or strips rolled into a condom, the strips being pulled to unroll the condom. It has been discovered that a major problem frequently arises when this condom is lubricated and the device is enclosed in a package. When the device is removed from the package the condom tends to unroll slightly, even when the utmost care is taken. If the device is removed from the package by pulling the strips or strands, premature unrolling of the condom is almost inevitable. By "premature unrolling" we mean a slight unrolling of the condom prior to its contact with the user's penis. The unrolling of the condom is itself not the problem.

Figure 1:
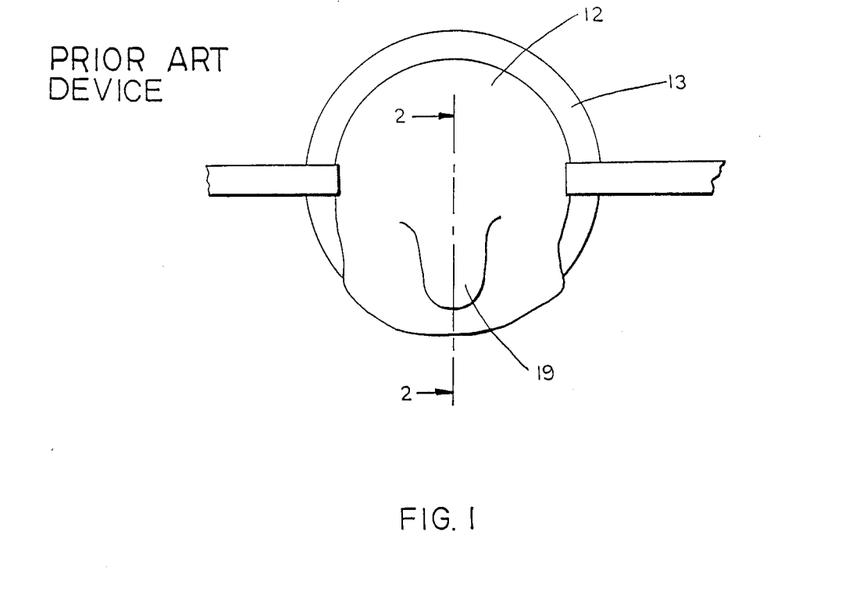
FIG. 1 is a plan view illustrating a problem frequently encountered when a prior art device is used in a certain manner.
Figure 2:
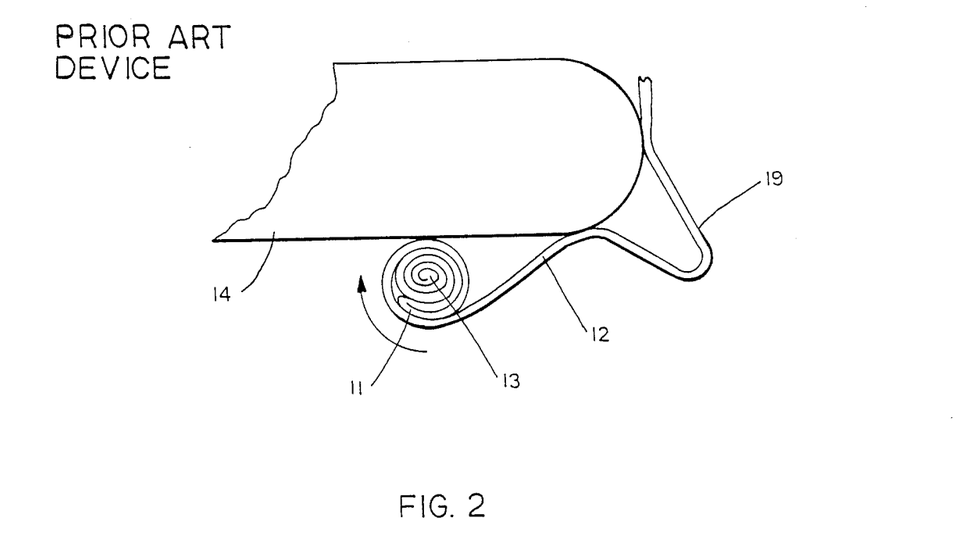
FIG. 2 is an enlarged fragmentary cross sectional view taken on line 2—2 of FIG. 1 further illustrating the problem solved or prevented by this invention, with portions of the device being greatly enlarged and crosshatching being omitted for clarity.

The problem that has been discovered, illustrated in FIGS. 1 and 2, is that when the condom unrolls prematurely, especially as it is being removed from the close confines of a package, the unrolled end of the condom tends, apparently because of the lubricant, to adhere to the rolled portion of the condom and then wrap around and become rolled into the rolled portion. This is best shown in FIG. 2, where a portion 11 of the unrolled end of the condom 12 has adhered to the rolled portion 13 and, as the rolled portion prematurely unrolled, has wrapped around and become rolled into the rolled portion 13. The tangled condom, now in contact with the user's penis 14, cannot be unrolled further and will tear before unrolling if additional force is applied to the strips. This problem, which occurs at a location between the strips, is prevented by the invention disclosed herein.

Referring now in detail to FIGS. 3–12 of the drawings, there is shown a "no hands" contraceptive device made up of a condom 12 and a pair of strips 17, the condom having a rolled portion 13 and a reservoir end 19. One end of each of the strips 17 is rolled into the rolled portion 13 of the condom 12. By "rolled into" we mean that the strips 17 are positioned to extend along opposite sides of the condom, prior to rolling, with one end of each strip being adjacent to the open end of the condom and then the condom and the strips are rolled together to form the rolled portion 13.

Figure 3:
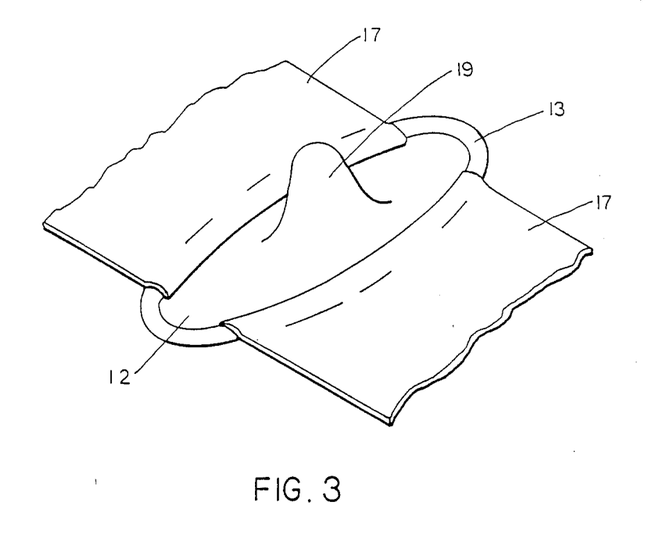
FIG. 3 is a perspective view showing the contraceptive device of this invention.
Figure 4:
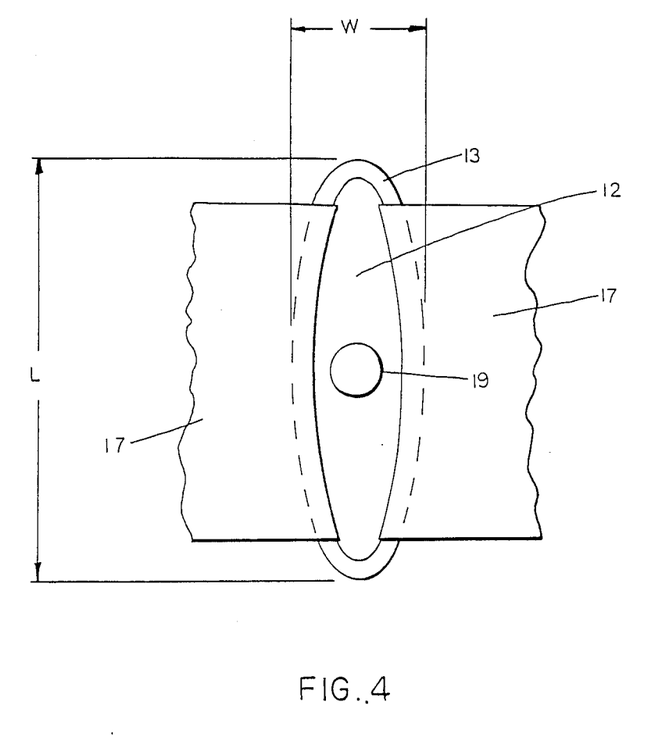
FIG. 4 is a plan view showing the generally elliptical configuration of the condom of this invention and the dimensions which determine the condom length to width ratio.

The strips 17 of this invention have a width which is sufficient to significantly change the configuration of the rolled portion 13 of the condom 12 from its normally circular configuration to a generally elliptical configuration, as best shown in FIGS. 3 and 4. The elliptical condom offers greater resistance to premature unrolling, so that the problem of tangling is substantially reduced or eliminated. It is believed that the elliptical condom is more difficult to unroll because to unroll it will require that significant compressive and tensile forces be applied to the inner and outer portions of the more sharply bent ends of the rolled portion 13.

The elliptical or non-circular configuration of the rolled portion 13 of the condom 12 can be quantified by expressing it in terms of a length to width ratio, which might also be referred to as an "out-of-round" ratio. The length and width dimensions of the non-circular condom are best illustrated in FIG. 4. The ratio of length (L) to width (W) of the rolled portion 13 of the condom 12 is at least 1.2 and preferably is at least 1.4. Most preferably, the L/W ratio is at least 1.6. This ratio is obtained by dividing the length of the generally elliptical rolled portion 13 by its width.

The L/W or out-of-round ratio of the rolled portion 13 is determined primarily by the width of the strips 17. Thickness, and consequently the cross sectional area of the strips, will have some effect on the L/W ratio. However, the range of thicknesses preferred for use is relatively small. Strips having a thickness of less than about 0.5 mils are more difficult to handle and manipulate while strips having a thickness greater than about 3 mils are more difficult to roll into the condom.

The thickness of the strips 17 should thus be about 0.5 to about 3.0 mils, with the preferred range for strip thickness being about 0.7 mils to about 2.0 mils. However, in view of the fact that the thickness range is small and the fact that for any thickness a certain minimum width is required to achieve the desired L/W ratio, the thickness of the strips 17 can be more or less ignored provided that the thickness is kept within a useful range. In this case, one would select a strip having a thickness within the most useful range, about 0.5 to 3.0 mils, and then make the strips of sufficient width to achieve the desired L/W ratio.

The condom 12 itself is a conventional, commercially available item. The strips 17 are made from a thin, flexible material which can be rolled into the condom. For example, a polymeric material such as polyethylene or other similar material may be used for making the strips 17. If the strips are cut from a polyethylene film or sheet it is preferred that the polyethylene not be highly oriented. Strips cut from softer, more easily stretched polyethylene sheets appear to give better results. It is believed that these sheets are less oriented than harder sheets which require more force to be stretched. For example, strips cut from bags labelled "tall kitchen garbage bags" (believed to be less oriented polyethylene) are superior to strips cut from plastic bags (believed to be more oriented polyethylene) used at grocery store checkout counters to bag groceries.

A support or backing sheet 22 and a cover sheet 23 are positioned on opposite sides of the condom to sandwich it therebetween (FIGS. 5-8). The sheets 22 and 23 may be made of a layer of paper bonded to a layer of thermoplastic material such as polyethylene.

Figure 5:
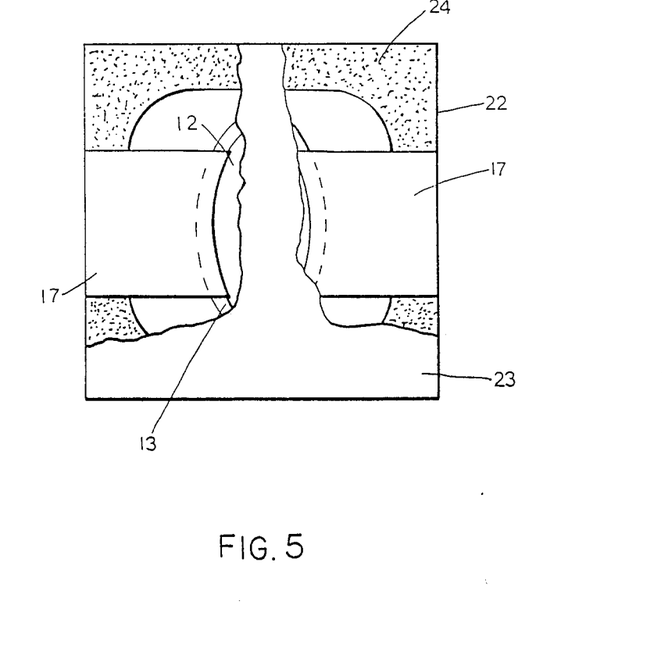
FIG. 5 is a fragmentary plan view of another embodiment of the invention Wherein a package is a part of the device.

The condom 12 is positioned between the sheets or layers 22 and 23 with the strips 17 extending outwardly to the edges of the sheets 22 and 23 as best shown in FIG. 5. Heat and pressure are applied to the edges of the sheets 22 and 23 to seal these edges together to form a hermetically sealed package for the condom. An area 24 extending around the edges of the sheets has been stippled in FIG. 5 to indicate that area where the sheets 22 and 23 are sealed together.

From FIG. 5 it can readily be seen that the strips 17 extend into the sealed area 24 and are adhered to the sheets 22 and 23 in this area. Thus, one can pull the strips 17 by tearing the package into two parts and then pulling the severed parts away from each other.

Figure 6:
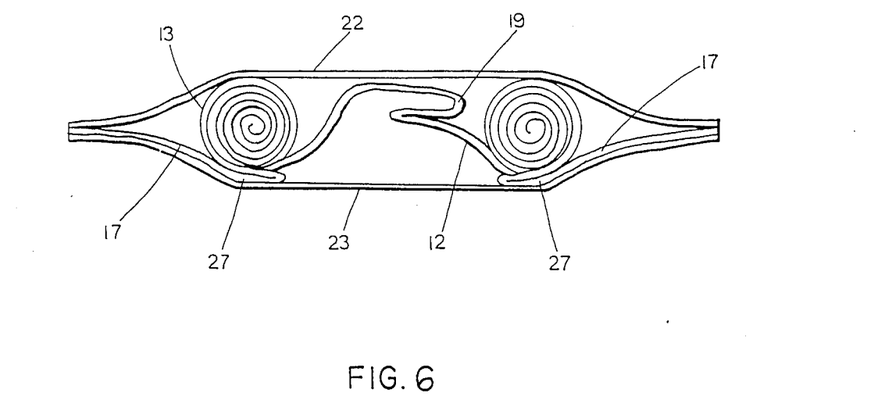
FIG. 6 is an enlarged cross sectional view showing the slack in the strips which allows the condom to be pulled from the package without premature unrolling, with crosshatching being omitted for clarity.
Figure 7:
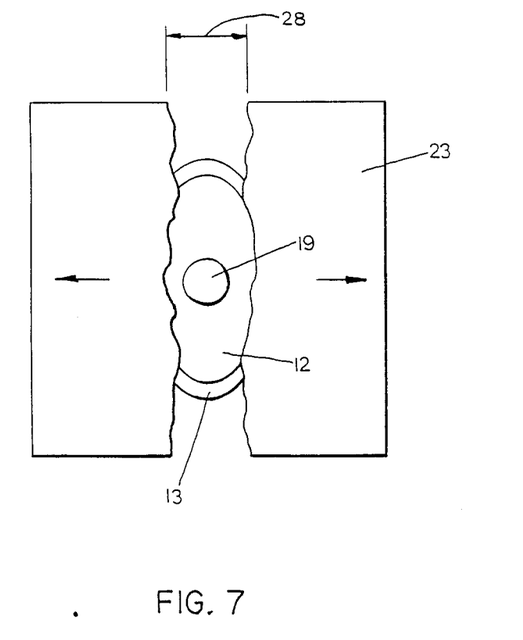
FIG. 7 is a plan view showing the structure of FIG. 5 after the package has been torn into two parts and the two parts have been separated sufficiently to pull the condom to an exposed position between the two parts of the package.
Figure 8:
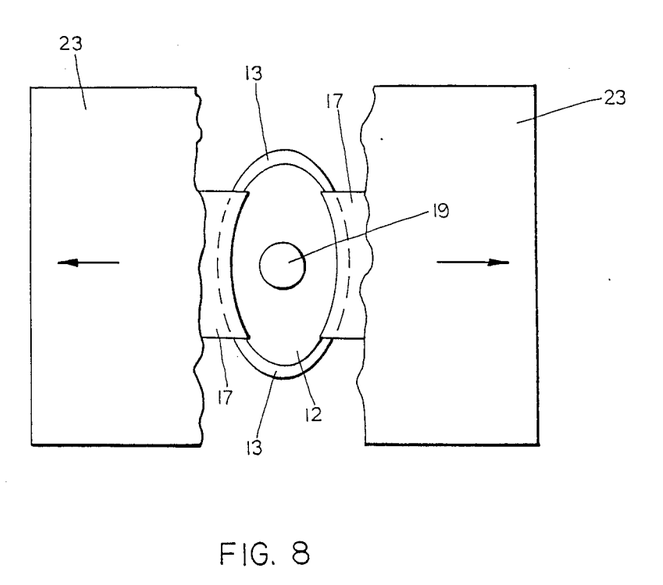
FIG. 8 is a plan view showing the structure of FIG. 7 after the condom has been pulled to a fully exposed position between the two parts of the package.

Those portions of the strips 17 extending from the rolled portion 13 to the sealed area 24 should have enough slack, indicated by reference numeral 27 in FIG. 6, that the two parts of the package can be pulled apart to bring the condom to an "exposed" position between the severed parts of the package, as shown in FIG. 7, before the rolled portion 13 begins to prematurely unroll. At this point the spacing, indicated by reference numeral 28 in FIG. 7, between the two parts of the package should be at least ⅛th of the diameter of the circular portion 13 rolled without strips. Preferably, the amount of slack in the strips 17 is great enough that the condom 12 can be pulled to a "fully exposed" position, i.e., the entire condom is visible, before premature unrolling occurs. This slack and other features which allow the condom to be pulled out of the package without premature unrolling are disclosed and claimed in copending application Ser. No. 300,139, filed Jan. 23, 1984 for "NO HANDS CONTRACEPTIVE DEVICE".

Figure 9:
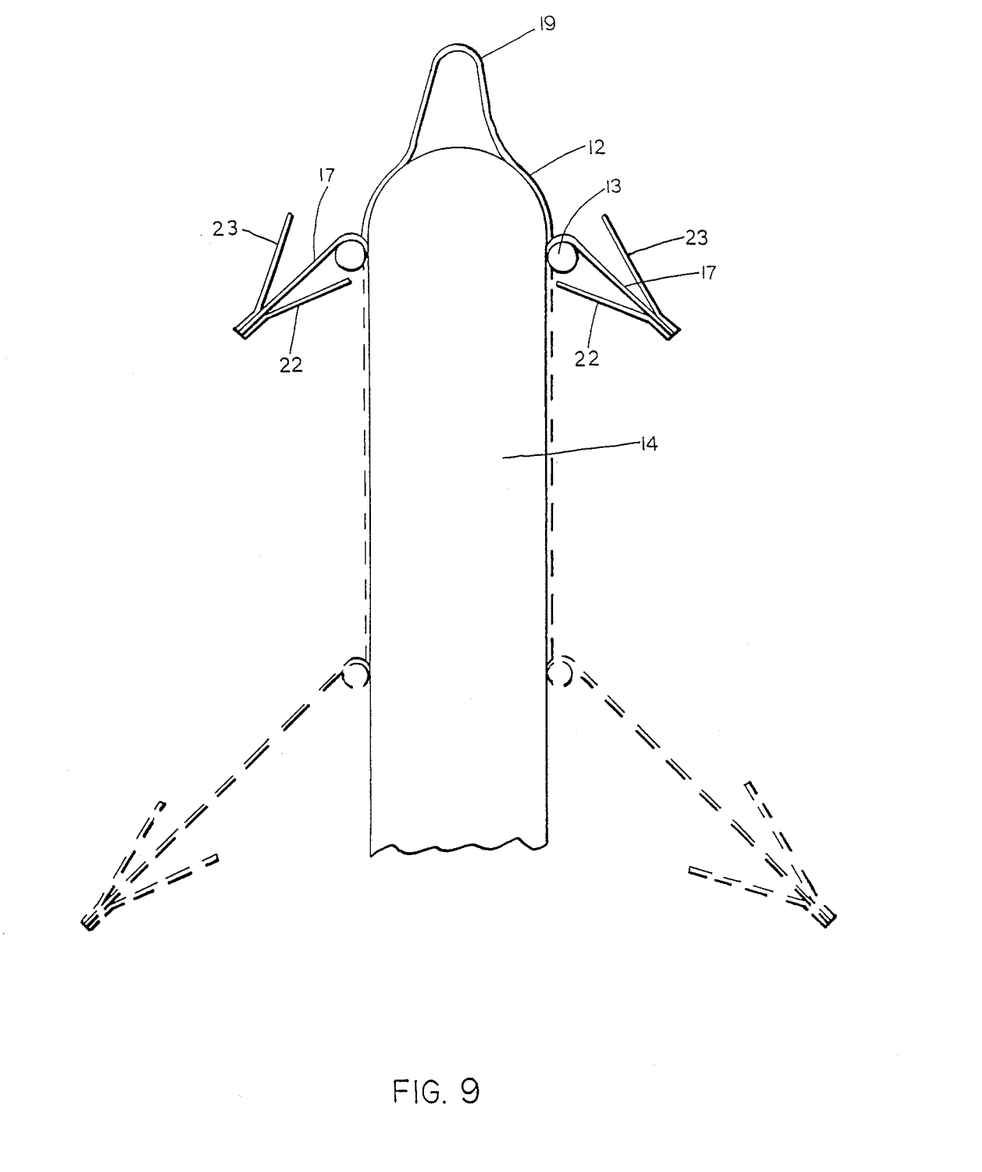
FIG. 9 is a schematic cross sectional view showing the manner in which the condom instantly unrolls onto the user's penis when the strips are pulled, With crosshatching being omitted for clarity.

FIG. 9 illustrates the operation of the device of this invention. The user tears the package into two parts and then pulls the two parts away from each other to bring the condom into the exposed position shown in FIG. 7. The user then places the condom against the end of the penis 14 and, holding the separated parts of the package, pulls the strips 17. Tension applied to the strips 17 causes the rolled portion 13 to unroll almost instantly onto the user's penis. It can readily be seen that the user need not touch any part of the condom with his hands.

Figure 10:
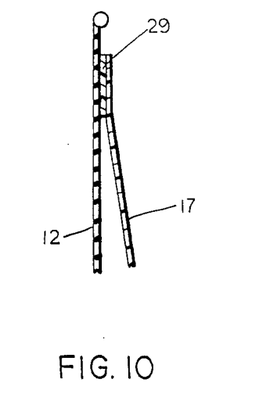
FIG. 10 is an enlarged fragmentary view showing the manner in which the ends of the strips may be attached to the condom.

When the end of the strips 17 are reached, the strips separate from the condom and may be discarded. However, if it is desired, the ends of the strips 17 may be secured to the condom. This is illustrated in FIG. 10, where an adhesive layer 29 is used to secure the strips 17 to the condom 12 such that the strips 17 remain attached to the condom after the rolled portion 13 is unrolled. The condo can be then removed merely by pulling the strips 17, so that the condom can be both put on and taken off without being touched by the user's hands.

If the rolled portion 13 is not unrolled completely when the condom is put on, such that a few turns of the strips 17 and the rolled portion 13 remain rolled, the condom can be pulled off as though the strips 17 were attached to the condom. The user merely pulls the strips 17 away from his body and the condom will be pulled off without further unrolling.

Figure 11A:
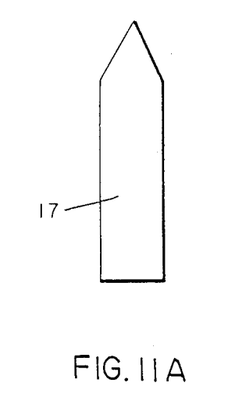
FIGS. 11A and 11B are side views showing two ways in which the ends of the strips may be tapered to facilitate the start of the rolling of the strips into the condom.
Figure 11B:
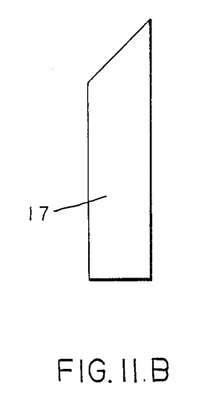

If the strips 17 are more than about one inch wide, it is preferred that the ends of the strips which are rolled into the condom be tapered as illustrated in FIGS. 11A and 11B. This will make it easier to begin the rolling of the strips and the condom.

While the invention is described above in terms of the out-of-round or L/W ratio, it can also be described in terms of the ratio of total strip width to circumferance of the rolled portion 13 of the condom. The sum of the Widths of the strips 17 is at least 20% of the length of the circumference of the rolled portion 13, the sum of the widths of the strips being the width of one strip added to the width of the other strip. Preferably, the sum of the widths of the strips is at least 30% of the length of the circumferance of the rolled portion 13 and, most preferably, is at least 40% of such circumference. An easy way to determine the circumference or periphery of the rolled portion is to measure the diameter of the rolled portion, rolled without the strips so that it is in its normal circular configuration, and then calculate the length of the circumferance.

EXAMPLE I

Figure 12:
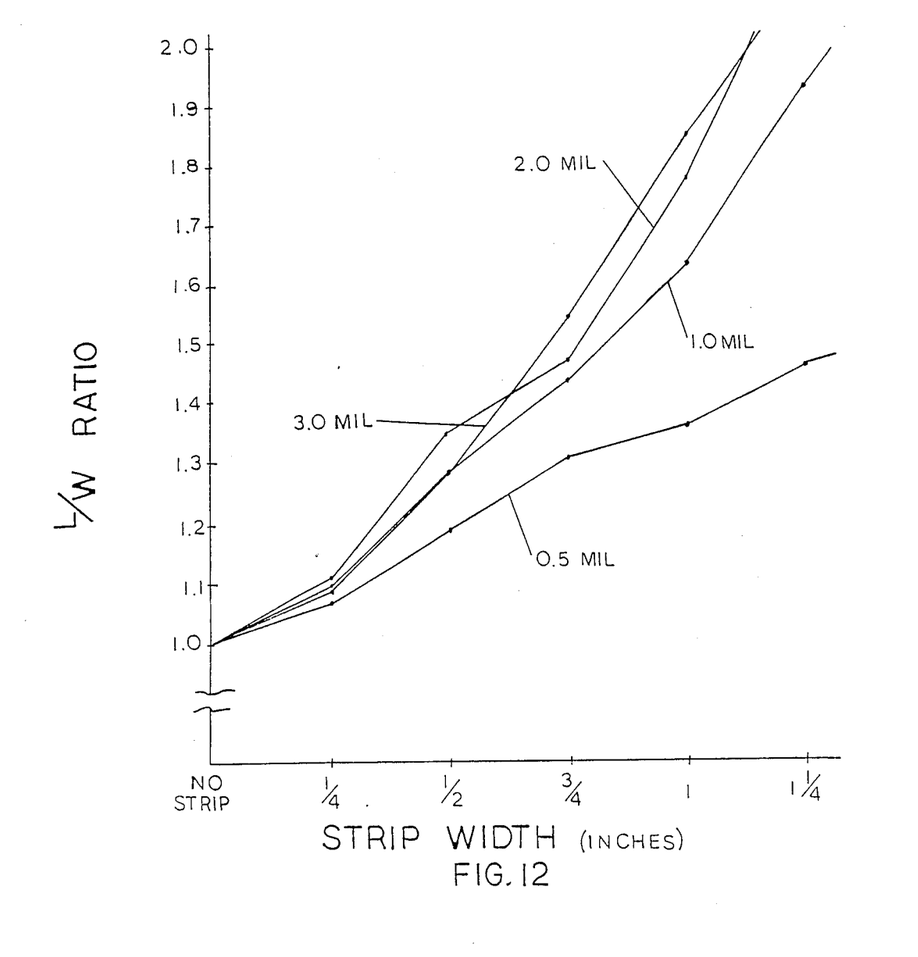
FIG. 12 is a graph showing the relationship between strip width, strip thickness and L/W ratio, with strips of various widths and thickness being represented.

Strips of different widths were cut from polyethylene films of different thicknesses and then rolled into condoms as described above. Strip thicknesses used were 0.5, 1.0, 2.0 and 3.0 mils. Strip widths were ¼", ½", ¾", 1" and 1¼". The L/W ratio of each condom was measured with strips of various widths and thicknesses rolled into the rolled portion 13. The results are shown in FIG. 12.

EXAMPLE II

The resistance of the condom to unrolling was determined by rolling strips into the condom, taping the end of one of the strips to the edge of a shelf and hanging a small envelope on the end of the other strip by the use of a paper clip. One cent coins were added, one at a time, to the envelope until the weight of the coins caused the condom to unroll. Strips of ¼", 1" and 1½" widths were cut from the same sheet of 0.7 mil polyethylene and rolled into the same condom. With the ¼" strips, the condom suddenly unrolled completely when ten coins were added to the enVelope. With the 1" strips, the condom slowly unrolled when 37 coins had been added to the envelope. With the 1½" strips, the paper clip pulled out of the strip when 161 coins had been added to the envelope. At this point the condom had not started to unroll.

The above was repeated using ¼", 1¼" and 1½" strips cut from a sheet of 2.0 mil polyethylene. With the ¼" strips, the condom unrolled completely when eight coins were added to the envelope. With the 1¼" strips, the condom did not unroll until 32 coins were added. With the 1½" strips, 200 coins were added to the envelope and the condom still had not begun to unroll.

What is claimed is:

1. A contraceptive device, comprising:
    a. a condom having a rolled portion, and
    b. a pair of strips each having one end thereof rolled into the rolled portion of the condom and the other end thereof extending from said rolled portion, said other ends of said strips being unconnected to each other, at least one of said strips having a width which is sufficient to cause the rolled portion of the condom to assume a generally elliptical configuration having a length to width ratio of at least 1.2 to increase the resistance of said rolled portion to premature unrolling, said rolled portion retaining said elliptical configuration without the influence of outside forces.

2. The device of claim 1 wherein said rolled portion has a length to width ratio of at least 1.4

3. The device of claim 1 wherein the strips are substantially the same width.

4. The device of claim 3 wherein the length to width ratio is at least 1.6.

5. The device of claim 3 wherein the thickness of the strips is within the range of 0.5 mils to 3.0 mils.

6. The device of claim 5 wherein the strips have a thickness within the range of 0.7 mils to 2.0 mils.

7. The device of claim 5 wherein the strips are made from polyethylene.

8. A contraceptive device, comprising:
    a. a condom having a rolled portion, and
    b. a pair of strips each having one end thereof rolled into the rolled portion of the condom on opposite sides thereof and the other end thereof extending from said rolled portion, said other ends of said strips being unconnected to each other, the sum of the widths of said strips being at least 20% of the length of the circumference of said rolled portion, said widths being measured at the widest portions of said strips.

9. The device of claim 8 wherein the sum of the widths of said strips is at least 30% of said circumference of said rolled portion, said widths being measured at the widest portions of said strips.

10. The device of claim 8 wherein said sum is at least 40% of said circumference.

11. The device of claim 8 wherein said one end of each strip is tapered.

12. The device of claim 8 wherein the ends of said strips are attached to the condom.

13. The device of claim 11 wherein the strips are made from polyethylene and have a thickness of 0.7 to 2.0 mils.

14. A contraceptive device, comprising
    a. backing sheet,
    b. a condom positioned on the backing sheet and having a rolled portion,
    c. a pair of strips positioned on opposite sides of the condom and each having one end thereof rolled into the rolled portion of the condom for unrolling the condom when the strips are pulled, the other ends of said strips being unconnected to each other and extending toward opposite sides of the backing sheet, the sum of the widths of said strips being at least 20% of the length of the circumference of said rolled portion, said strips being measured at the widest portions of said strips, and
    d. a cover sheet secured to the backing sheet to enclose the condom therebetween.

15. The device of claim 14 wherein the sum of the widths of said strips is at least 40% of the length of the circumference of said rolled portion of said condom, said widths being measured at the widest portions of said strips.

16. The device of claim 14 wherein said other ends of said strips extend to and are secured to the edges of the sheets and are provided With sufficient slack that the sheets can be torn into two parts and the condom pulled to an exposed position between said two parts without premature unrolling of said condom.

17. The device of claim 14 wherein said rolled portion has a generally elliptical configuration having a length to width ratio of at least 1.2.

18. The device of claim 16 wherein the strips are made from polyethylene and have a thickness of about 0.5 to about 3.0 mils.

* * * * *

UNITED STATES PATENT AND TRADEMARK OFFICE
CERTIFICATE OF CORRECTION

PATENT NO. : 4,972,850
DATED : November 27, 1990
INVENTOR(S) : Robert L. Broad, Jr.

It is certified that error appears in the above-identified patent and that said Letters Patent is hereby corrected as shown below:

Column 2, line 4, "Wherein" should read --wherein--.

Column 2, line 20, "With" should read --with--.

Column 4, line 37, "1984" should read --1989--.

Column 4, line 56, "condo" should read --condom--.

Column 5, line 7, "Widths" should read --widths--.

Column 5, line 41, "enVelope" should read --envelope--.

Column 6, line 58, "With" should read --with--.

Signed and Sealed this

Eighteenth Day of February, 1992

*Attest:*

HARRY F. MANBECK, JR.

*Attesting Officer*      *Commissioner of Patents and Trademarks*